United States Patent [19]

Mori et al.

[11] Patent Number: 5,233,860
[45] Date of Patent: Aug. 10, 1993

[54] WATER MEASURING SYSTEM WITH IMPROVED CALIBRATION

[75] Inventors: Takeshi Mori; Hiromi Ohkawa; Satoshi Kohno, all of Kyoto, Japan

[73] Assignees: Horiba, Ltd., Kyoto; Tasco Japan Co., Ltd., Osaka, both of Japan

[21] Appl. No.: 815,279

[22] Filed: Dec. 27, 1991

[30] Foreign Application Priority Data

Dec. 30, 1990 [JP] Japan .................... 2-416956
Jan. 16, 1991 [JP] Japan .................... 3-4534[U]

[51] Int. Cl.$^5$ .................... G01N 33/18; G01N 27/00
[52] U.S. Cl. .................... 73/1 G; 73/19.1; 436/8
[58] Field of Search .................... 436/8, 9; 73/19.01, 73/19.1, 16, 1 R

[56] References Cited

U.S. PATENT DOCUMENTS

| | | | |
|---|---|---|---|
| 3,942,792 | 3/1976 | Topol | 73/19.1 |
| 4,330,385 | 5/1982 | Arthur et al. | 73/19.1 |
| 4,689,308 | 8/1987 | Gerhard | 436/8 |
| 4,779,446 | 10/1988 | Rowland | 73/1 G |
| 4,914,424 | 4/1990 | Hirao et al. | 73/1 G |
| 5,008,616 | 4/1991 | Lauks et al. | 73/1 R |
| 5,022,980 | 6/1991 | Tanaka et al. | 73/1 R |
| 5,061,631 | 10/1991 | Calabrese | 73/1 R |
| 5,124,659 | 6/1992 | Frola et al. | 73/1 R |

FOREIGN PATENT DOCUMENTS

| | | |
|---|---|---|
| 0220666 | 10/1986 | European Pat. Off. . |
| 0417571A1 | 8/1990 | European Pat. Off. . |
| 0171448 | 9/1985 | Japan .................... 73/19.01 |
| WO8501579 | 4/1985 | PCT Int'l Appl. . |
| WO9001160 | 2/1990 | PCT Int'l Appl. . |
| 2219398A | 5/1989 | United Kingdom . |

*Primary Examiner*—Hezron E. Williams
*Assistant Examiner*—George Dombroske
*Attorney, Agent, or Firm*—Price, Gess & Ubell

[57] ABSTRACT

A water measuring system for measuring different parameters of water having a compact configuration that can be easily calibrated is provided. A plurality of individual sensors, are mounted on the housing, including a dissolved oxygen measuring sensor that can be mounted at a position separate from the other sensors. A hood member can be mounted at the lower end of the housing member to protect the sensors. A container that is capable of holding a calibration liquid can be fitted onto the housing member to provide the liquid at a position that will only contact those sensors other than the oxygen measuring sensor during a single calibration procedure.

19 Claims, 6 Drawing Sheets

WATER MEASURING SYSTEM WITH IMPROVED CALIBRATION

BACKGROUND OF THE INVENTION

1. Field of the Invention

The present invention is directed to a water measurement system for measuring various properties of water and, more particularly, to an improved water measurement system having a configuration to optimize calibration procedures.

2. Description of Related Art

With the increased emphasis on monitoring environmental conditions, there is a specific demand to provide efficient and economical apparatus to measure the quality of water. Issues, such as acid rain and industrial pollution, need to be quantified by appropriate measurements and instruments have been devised for measuring the water quality of, for example, rivers, by measuring different parameters of the water, such as its pH, dissolved oxygen content, conductivity and turbidity. To facilitate the ease of such measurements, a water quality checker or water measuring instrument has been suggested that has a number of different kinds of measuring sensors to enable the respective measurements to be performed in one operation. When utilizing such an instrument, it is necessary to calibrate the respective measuring sensors prior to an actual measurement to ensure accurate readings. Such calibrations have usually involved providing a calibrating liquid, such as a solution of phthalate, placed into a beaker with the measuring instrument then immersed into the solution in the beaker. The individual measuring sensors, other than a dissolved oxygen measuring sensors, can usually be calibrated by the use of a standard of phthalate in one operation. However, to calibrate the dissolved oxygen measuring sensor, it is usually necessary to saturate this calibrating solution with air, and this is generally done by bubbling air into the solution and conducting the calibration after a saturated state has been achieved. Each of the measuring sensors is then immersed in the calibration solution at one time to carry out the calibration of the respective measuring sensors. In order, however, to obtain an accurate measured value in the case of the dissolved oxygen measuring sensor, it is necessary to provide a movement of the fluid to some extent across this sensor. To achieve this flow rate, the standard solution has been frequently stirred during the calibration to accomplish this purpose.

As can be readily determined, the additional calibrating steps of bubbling air into the calibrating solution and stirring the solution is not necessary for calibrating the other individual sensors. These requirements add to the complexity and time period required in a calibration operation. These requirements also increase the size of the water measuring apparatus, even though the modern trend is to try and provide compact instrumentation.

Thus, there is a demand in the prior art to simplify a water measurement system that must be calibrated to accommodate a plurality of kinds of measuring instruments, including a dissolved oxygen measuring sensor and to enable less skilled operators to use the instrument.

SUMMARY OF THE INVENTION

The present invention provides an improved configuration of a water measuring apparatus and a system for calibrating the same.

A compact housing member mounts a plurality of individual sensors at a lower portion of its housing with an oxygen measuring sensor mounted on the housing member at a position above and apart from each of the other sensors. A container, configured to interface with the housing member, can hold a liquid, such as an aqueous solution of phthalate and can be connected to the housing member. The container can be basically cylindrical in configuration and can be further configured to be aligned with and exclude the oxygen measuring sensor from contact with the calibrating liquid. The individual sensors can include a pH-measuring electrode, a reference electrode, a conductivity cell or sensor, and a turbidity cell or sensor.

In addition, an auxiliary hood member can be removably mounted to the housing member and extended downward from the housing member to encompass each of the individual sensors. The hood member can have an outer cylindrical configuration with an indented portion that will be complementary to the container holding the calibrating liquid solution. Instrumentation for calculating the properties of the water can be connected through a cable with an appropriate display screen.

Alternative embodiments of the container can be utilized, such as a cylindrical configuration with a hollow post positioned to be aligned with the oxygen sensor.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DESCRIPTION OF THE PREFERRED EMBODIMENT

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide a water measuring system with an improved calibration procedure.

Figure 1:
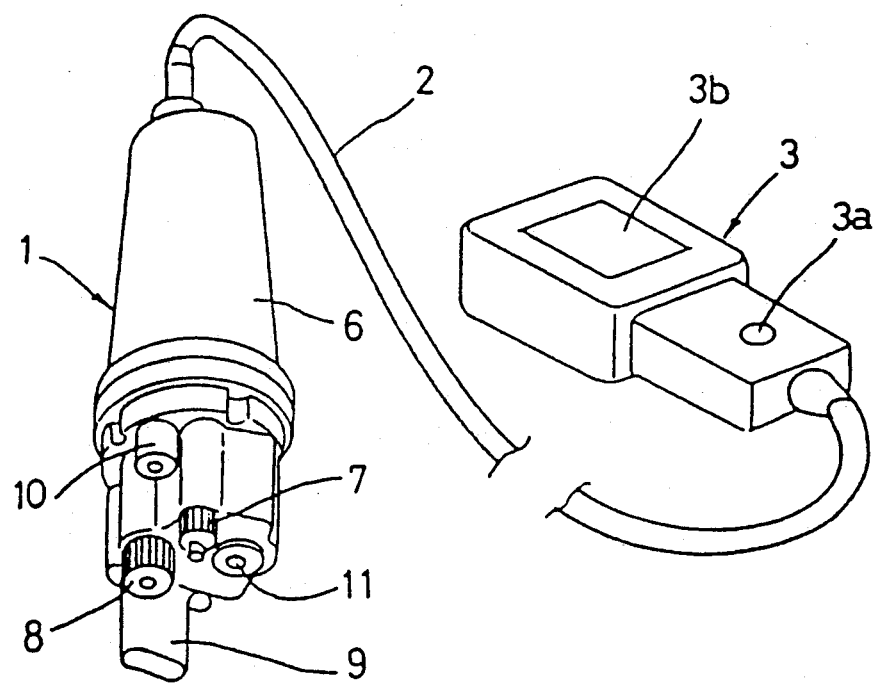
FIG. 1 is a perspective view of one embodiment of a water measuring system of the present invention.
Figure 1:
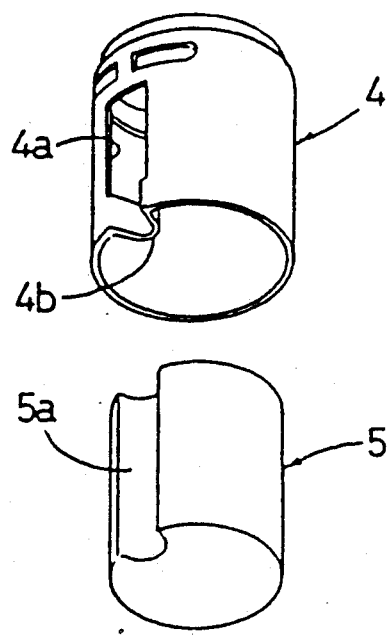

Referring to FIG. 1, a perspective view of the first embodiment of a water measurement system according to the present invention is disclosed wherein a compact sensor member 1 is electrically connected through an appropriate cable to a monitor and display system 3. The compact housing member 6 mounts at its lower end a plurality of individual sensors. A protecting hood member or shielding tube 4 with an open bottom can be detachably mounted on the lower end portion of the sensor housing member 6, for example, by a bayonet structure. The hood member 4 is provided with a side opening 4a and a guide member 4b projecting on an intercircumferential side of a cylindrical configuration. A calibration container 5 has a roughly cylindrical enveloping exterior wall and is provided with a grooved indent or partition portion wall 5a which is complementary to the guide member 4b. The sensor member 1 has mounted on its housing 6 adjacent its circular lower end portion, a plurality of individual water quality sensors. Such sensors can include a pH-measuring glass electrode 7, a reference electrode 8, a conductivity cell or sensor 9 for measuring the conductivity of the water, a dissolved oxygen (DO) measuring sensor 10 for measuring dissolved oxygen and a turbidity cell or sensor 11 for measuring the turbidity of the water. As can be seen the DO sensor 10 is arranged at a position closer to a circumferential portion of the lower end surface of the housing member.

These respective individual sensors can have their outputs electrically connected through the cable 2 to the monitor 3. As shown in FIG. 1, an operator button 3a can be utilized to activate the instrument and operational results can be displayed on a display portion 3b, such as a liquid crystal display. This monitor can incorporate a microprocessor chip and appropriate circuitry for converting the analog inputs from the various sensors into a digital input and calculating the measured parameters of the waters. Such circuits in monitors are known and conventional and accordingly a description of the same is omitted here.

The monitor 3 also is utilized in the calibration procedure to enable a calibration of each of the individual sensors, preferably at a simultaneous operation by activation of a single switch. This calibration operation can be automatically carried out when the operator inserts the sensor member 1 into the calibration container 5 with the phthalate solution and presses a calibration switch so that the reference values that have been programmed into the microcomputer can be recalibrated, as is known in the sensor field.

The protective hood or tube 4 has basically an approximate cylindrical shape and is dimensioned to surround the respective measuring sensors provided in the lower end portion of the housing member 6 to protect the measuring sensors from shocks. The positioning of the opening 4a and guide member 4b is arranged to correspond to and complement the positioning of the DO sensor 10 on the lower portion of the housing member 6.

The calibration container 5 also has an approximate cylindrical configuration and its indented portion also is appropriately positioned to coordinate and complement the positioning of the DO sensor 10. The partition wall portion 5a forms a complementary groove to the indented portion or guide member 4b of the protecting hood or shield tube 4. When the calibration container 5, containing an appropriate calibrating liquid, such as an aqueous solution of phthalate with a pH of 4, is mounted within the hood member 4, the DO sensor 10 will reside within the groove 5a and be isolated from the internal space or cavity of the calibration container 5. Reference can be made to FIG. 3 to disclose the relationship between the DO sensor 10 and the other individual sensors. As can be seen, the liquid level of the calibrating solution is represented by the broken line 12 in FIG. 3 and can be further seen in FIG. 2. This liquid level is sufficient to encompass and immerse each of the individual sensors with the exception of the DO sensor 10 for calibration purposes.

Since it is still desirable for the DO sensor 10 to be calibrated, the calibration values have now been established for calibrating the DO sensor 10 directly in an air environment, as opposed to being calibrated in an oxygen saturated liquid. This removes the necessity of requiring the bubbling of oxygen or air into the calibration solution and the subsequent stirring of the solution to create a flow rate across the DO sensor 10. Thus, by isolating the DO sensor 10, a single calibration step can be performed in a highly efficient manner, while maintaining a compact configuration to the water measuring apparatus. As can be appreciated, the operator controls, mounted on the monitor 3, can also be simplified so that a simultaneous calibration of each of the individual sensors, including the dissolved oxygen sensor 10, can be accomplished.

Figure 2:
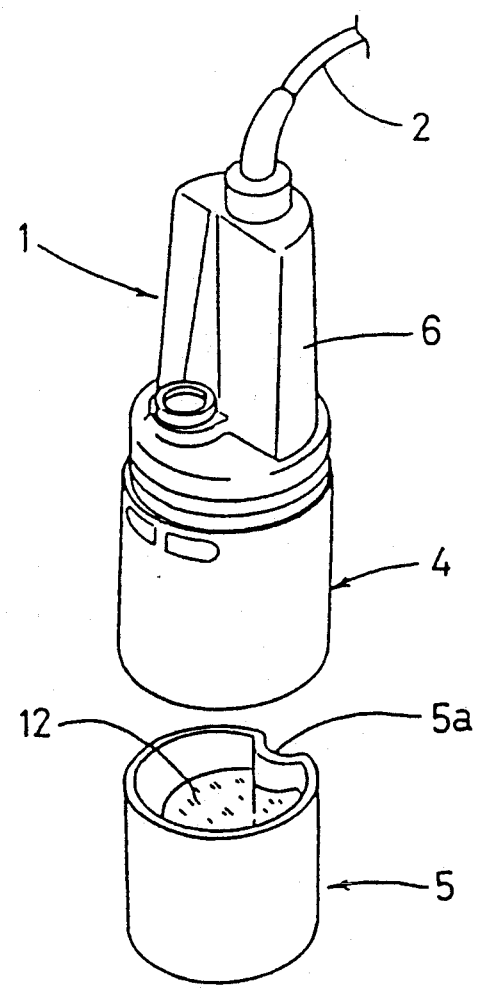
FIG. 2 is a perspective view of the first embodiment of the water measuring system with a container filled with a calibration solution.
Figure 3:
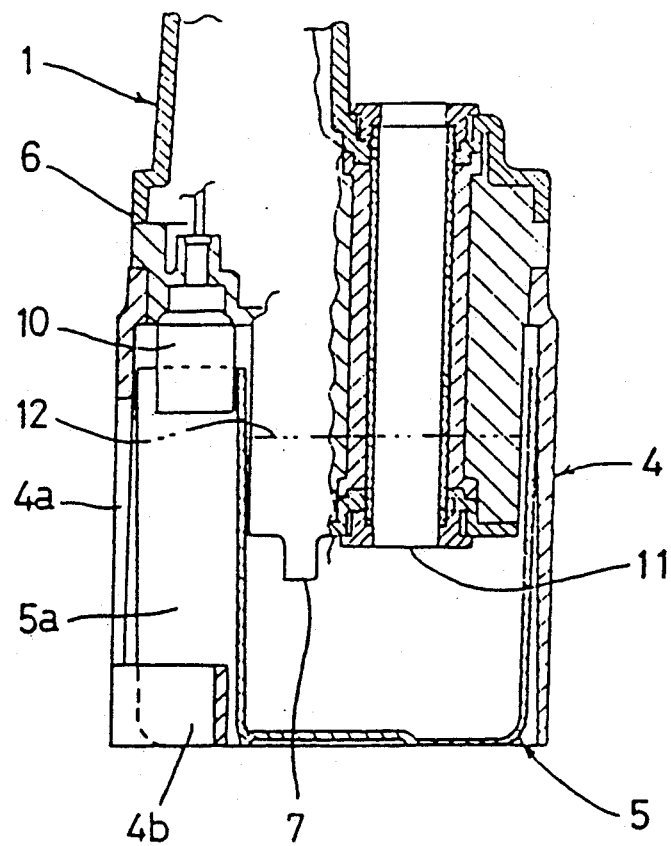
FIG. 3 is a partial cross-sectional view of the first embodiment of the water measurement system.

Referring to FIGS. 2 and 3, the operating procedures in establishing the calibration of the water measurement system of the present invention is accomplished as follows.

The hood member or protecting tube 4, mounted at the lower end portion of the housing member 6, includes an indented guide portion 4b. The cylindrical calibration container 5, having the grooved surface 5a, can be filled with an aqueous solution of phthalate having a pH of 4. The operator can then upwardly insert the calibration container 5 utilizing the indented guide portion 4b and the groove 5a for alignment purposes until the container 5 is fully inserted within the hood member 4. As can be seen from FIG. 3, the DO sensor 10 is positioned at the upper portion of the groove 5a and exterior from the liquid containing calibration container 5. In this position, the DO sensor 10 is exposed only to air and is not subject to the calibrating liquid. Each of the other individual sensors, however, are immersed within the calibrating liquid within the calibration container 5.

At this point, the operator can then initiate a single calibration step wherein the DO sensor 10 will detect a concentration of oxygen in the atmosphere and this atmospheric air will serve as a standard gas for calibrating the oxygen sensor. As a result of this calibration, a reference point for the DO sensor 10 will be established. Simultaneously, the calibration of the other immersed individual sensors is carried out in the same manner as in the conventional water quality check instruments on the basis of their signals detected relative to the aqueous phthalate solution. As can be immediately appreciated, this simple and single calibration step removes the required bubbling treatment and stirring action that has been previously required in the calibration of the DO sensor 10. Additionally, the position of the DO sensor 10 is still conveniently packaged in the same housing member 6 as the other individual sensors for ultimate utilization for checking the quality of water.

The opening 4a in the hood member adjacent the positioning of the DO sensor 10 within the groove 5a ensures that the DO sensor 10 will be sufficiently exposed to air during the calibration procedure.

The protecting tube or hood member 4 can also provide a further function, since it can act as a stand or support member when the sensor instrument I is placed on the floor or on a support surface and thereby protects the individual sensor elements.

Figure 4:
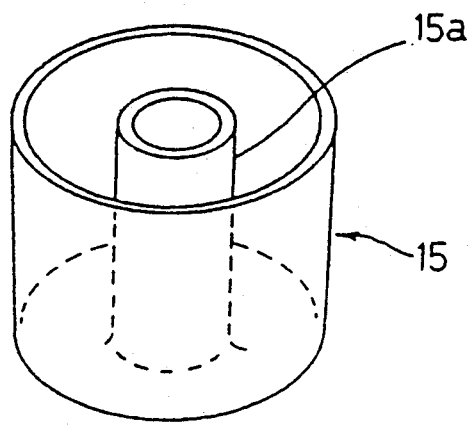
FIG. 4 is a perspective view of an alternative container for housing calibration liquid.
Figure 5:
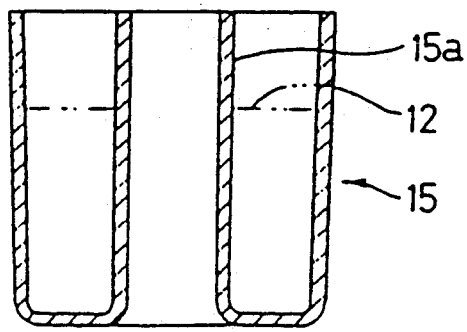
FIG. 5 is a cross-sectional view of FIG. 4.

Referring to FIGS. 4 and 5, an alternative embodiment of a calibration container 15 is disclosed. In this embodiment, the calibration container 15 is provided with a cylindrical inner circumferential wall which is used as a partition wall portion wall 15a for isolating a DO sensor 10 outside of the calibration container 15. In this regard, the DO sensor 10 would be positioned at a central portion of the housing member. The other measuring sensors are arranged around the DO sensor 10 so that they would fit within the cavity of the calibration container 15. As a result, the DO sensor 10 will be exposed to air while the other measuring sensors will be immersed in the standard calibration solution 12. The same single calibration procedure can be used with this embodiment as with previous embodiments shown in FIGS. 1 through 3.

As shown in FIG. 3, by positioning the DO sensor 10 vertically above the other individual sensors and, more particularly, at a position that would be higher than the liquid level of the standard solution 12 within either of the calibration containers 5 or 15, it is possible to further ensure that the DO sensor will only be subject to a calibration fluid consisting of only the atmospheric air. Additionally, if a calibration container is not available, a careful immersion of the other sensors in the calibrating liquid, while keeping the liquid level below the DO sensor 10, will still permit an appropriate calibration of the instrument. Thus, while it is preferred to use a calibration container configured to exclude the DO sensor 10 from the internal portion of the container. It can be seen that an alternative container holding calibration liquid can also be utilized, as long as the liquid is at a position that will only contact the individual sensors other than the oxygen measuring sensor.

Figure 6:
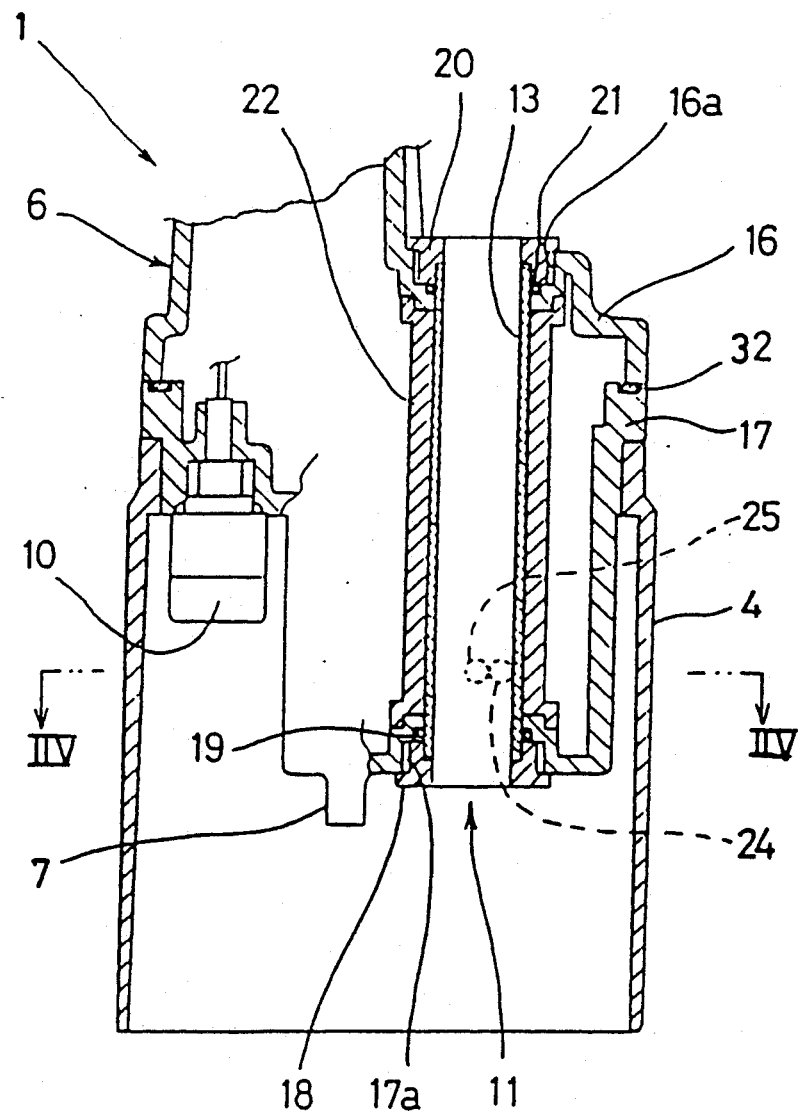
FIG. 6 is a cross-sectional view of an alternative embodiment of a housing member for a water measurement system.
Figure 7:
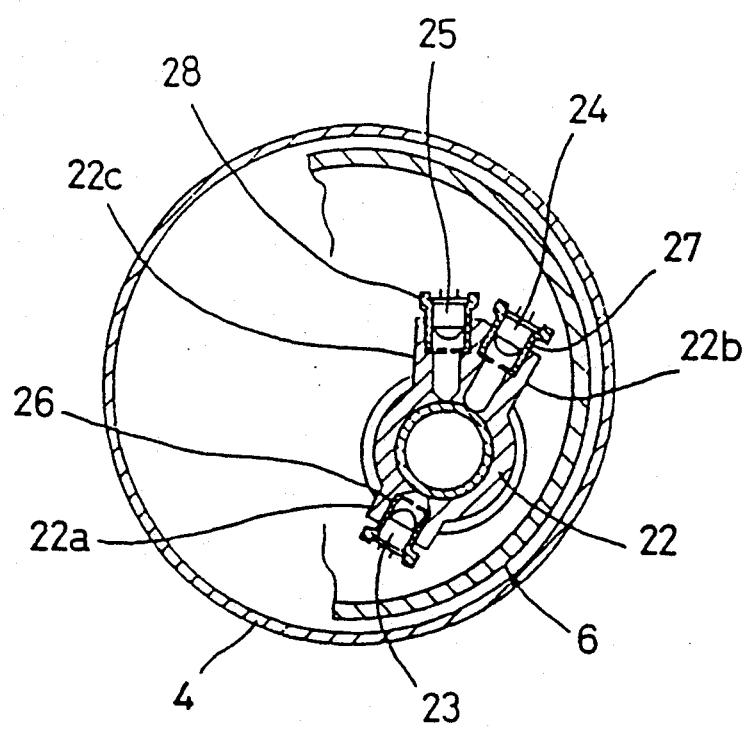
FIG. 7 is a partial traverse view of FIG. 6 taken along the lines VII—VII.

Another embodiment of the present invention disclosing a cylindrical hood member and a dissolved oxygen sensor positioned at a higher level than the other individual sensors is disclosed in FIGS. 6 and 7. The sensor body 6' comprises an upper frame 16 and a lower frame 17. The interface or joint between these respective frames can be sealed with an appropriate O-ring 32. The sensor member body 16 is further provided with a cylindrical glass tube 13 having an upper end and a lower end. This glass cylindrical tube is transparent and forms a cavity for the turbidity cell 11' which vertically passes through the upper frame to the lower frame. The glass tube 13 can be fixed by means of a lower fixing screw 18 that can capture the lower end of the glass tube 13. The screw 18 can be mounted in a threaded concave portion 17a of the lower frame 17. An O-ring 19 can be positioned between the upper end of the lower fixing screw 18 and the housing portion 17a of the lower frame 17 to seal the lower end portion of the glass tube 13 with the lower frame 17. At the upper portion of the glass tube 13, an upper fixing screw 20 can also be screwed into a concave recessed portion 16a of the upper frame 16. Thus, the glass tube 13 will be captured between the respective fixing screw members. These fixing screw members can be annular rings and could, as desired, be threaded into the frame 16. Again, an O-ring 21 is positioned between the lower end of the upper screw member 20 and the concave portion 16a of the upper frame 16 to seal the upper portion of the glass tube 13 to the upper frame 16. A ring-enforcing tube member 22 can be positioned about the glass tube 13 and can provide traversely mounted cylindrical tube openings 22a, 22b and 22c, as shown in FIG. 7. These openings are provided at predetermined angles about the glass tube and the cylindrical member 22a can be provided with an LED light source 23, while the lateral cylindrical member 22b is provided with a photodetector 24 as a transmitted light receiving element. The lateral cylindrical member 22c is further provided with a separate photodiode 25 as a scattered light receiving element. The LED 23, photodiode 24 and photodiode 25 can be secured with cap members 26, 27, 28, respectively, that are mounted with an integral mask or slit portion to define the light path both transmitted into the glass tube 13 and received by the respective detectors.

By providing this particular configuration with the opening at the upper portion of the glass tube 13, the turbidity measuring cell 11' of this embodiment can enable the calibrating fluid to vertically rise within the glass tube 13 as air egresses from the upper end of the glass tube 13. The fluid is designed to extend above the location of the LED and respective photodiode sensors, as shown by the dotted lines in FIG. 6. As a result, liquid can be subject to the transmission of the light and the transmitted and scattered light can be detected to determine the turbidity of the water while still enabling the DO sensor 10 to remain above the level of the sampling water. As can be readily appreciated, an outside indicia marker can be provided to establish an immersion level of the hood 4' in the calibration liquid, or the hood 4' can be transparent to facilitate enabling the appropriate calibration liquid level within the hood member and below the DO sensor 10'.

The operation of the turbidity cell is of a known procedure wherein light beams transmitted through the sample liquid from the LED 23 are received respectively by the transmitted light receiving photodiode 24, while the scattered light beams resulting from the calibrated sample liquid are received by the scattered light receiving photodiode 25. The turbidity of the sample liquid is measured from a ratio of the quantity of the transmitted light to that of the scattered light in a conventional manner.

By positioning the turbidity measuring cell 11 in a vertical manner within the sensor body 6', a compact configuration can be maintained without eliminating the arrangement of the other individual measuring sensors. Additionally, the inside portion of the glass tube 13, in which the sample liquid will enter and which further forms the cell window of the turbidity measuring cell 11', constitutes a smooth and continuous circumferential surface so that the bubbles, dirt and stains that can occur during the use of the water measuring apparatus will be reduced to a minimum and can be subject to an easy cleaning step.

As an additional feature, the configuration of the turbidity cell 11' would lend itself to directly measuring the turbidity of a fluid in a continual manner by attaching a sample liquid tube at one end of the glass tube 13 and a sample liquid discharging tube at the other end, whereby the turbidity cell can be utilized as a flow cell for a continuous measuring of any sample liquid.

The present invention has been specifically designed to provide a relative compact and convenient water measuring apparatus that can be simply calibrated in one simultaneous step. The dissolved oxygen measuring sensor is, in each of the embodiments, only exposed to air while the other individual measuring sensors can be immersed within a standard calibration solution. A calibration container of a specific design can interface with the sensor housing. Alternatively, a hood member can be utilized to protect the individual sensors while enabling the immersion of the individual sensors other than the dissolved oxygen measuring sensor. The dissolved oxygen measuring sensor is preferably positioned at a vertical level above the other sensors so that calibration of the entire water measurement apparatus can be accomplished without requirement of the additional steps of bubbling and stirring a calibration solution.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A water measurement apparatus for measuring different parameters of water comprising:
   a housing;
   a plurality of individual sensors mounted on the housing, including an oxygen measuring sensor, the oxygen measuring sensor being mounted at a position separate from the other sensors, and
   means for enabling a calibration of the sensors other than the oxygen measuring sensor, including a container for providing a liquid at a position that will only contact the sensors other than the oxygen measuring sensor, wherein the container is configured to extend around the oxygen measuring sensor.

2. A water measurement apparatus as in claim 1 wherein the container is configured to exclude the oxygen measuring sensor from contacting the liquid.

3. A water measurement apparatus as in claim 1 wherein the container is cylindrical.

4. A water measurement apparatus as in claim 1 wherein the plurality of individual sensors other than the oxygen measuring sensor are mounted below the oxygen measuring sensor.

5. A water measurement apparatus as in claim 1 further including a cylindrical hood member extending below the individual sensors.

6. A water measurement apparatus as in claim 3 wherein the cylindrical container has an indented periphery configured so as to exclude the oxygen measuring sensor.

7. A water measurement apparatus as in claim 3 wherein the cylindrical container includes a central protruding tube configured so as to extend about the oxygen measuring sensor.

8. A water measurement apparatus as in claim 4 wherein said plurality of individual sensors includes a pH-measuring electrode, a conductivity cell, and a turbidity cell.

9. A water measuring apparatus as in claim 8 wherein the liquid for calibration is an aqueous solution of phthalate with a pH of 4.

10. In a water measurement system for measuring several parameters of water with a plurality of individual sensors mounted on a common housing, the improvement comprising:
    a housing member mounting a plurality of individual sensors at a lower portion of the housing;
    an oxygen measuring sensor mounted on the housing member at a position above each of the other sensors;
    a calibrating liquid capable of calibrating the individual sensors mounted below the oxygen sensor, and
    a container configured to interface with the housing member and holding the calibrating liquid in such a manner as to extend operatively about the individual sensors except for the oxygen sensor.

11. A water measurement apparatus as in claim 10 further including a cylindrical hood member extending below the individual sensors and the oxygen sensor.

12. A water measurement apparatus as in claim 10 wherein the container has an indented periphery of a configuration to exclude the oxygen measuring sensor to its outside.

13. A water measurement apparatus as in claim 10 wherein the container includes a central protruding tube configured so as to extend about the oxygen measuring sensor.

14. A water measurement apparatus as in claim 10 wherein said plurality of individual sensors includes a pH-measuring electrode, a conductivity cell, and a turbidity cell.

15. A water measuring apparatus as in claim 14 wherein the liquid for calibration is an aqueous solution of phthalate with a pH of 4.

16. In a water measurement system for measuring several parameters of water with a plurality of individual sensors mounted on a common housing, the improvement comprising:
    a housing member mounting a plurality of individual sensors at a lower portion of the housing;
    an oxygen measuring sensor mounted on the housing member at a position above each of the other sensors;
    a hood member removably mounted to the housing member and extending downward from the housing member to encompass each of the individual sensors, and
    a container configured to interface with the housing member and to extend within the hood member, the container is further configured to hold liquid within its central portion and to have a perimeter enveloping wall which excludes the oxygen measuring sensor, whereby, when a calibrating liquid is inserted within the container, it can operatively contact each of the individual sensors with the exception of the oxygen measuring sensor.

17. A water measurement system as in claim 16, wherein said plurality of individual sensors includes a pH-measuring electrode, a reference electrode, a conductivity cell, and a turbidity cell.

18. A water measurement system as in claim 17, wherein the hood member and the container have an indented configuration aligned with the oxygen measuring sensor.

19. A water measurement system as in claim 18, further including an aqueous solution of phthalate as a calibration liquid.

* * * * *